United States Patent
Pudil et al.

(10) Patent No.: US 10,960,381 B2
(45) Date of Patent: Mar. 30, 2021

(54) ZIRCONIUM PHOSPHATE DISINFECTION RECHARGING AND CONDITIONING

(71) Applicant: Medtronic, Inc., Minneapolis, MN (US)

(72) Inventors: Bryant J. Pudil, Plymouth, MN (US); Christopher M. Hobot, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 376 days.

(21) Appl. No.: 15/958,337

(22) Filed: Apr. 20, 2018

(65) Prior Publication Data

US 2018/0361354 A1 Dec. 20, 2018

Related U.S. Application Data

(60) Provisional application No. 62/519,933, filed on Jun. 15, 2017.

(51) Int. Cl.
*B01J 20/34* (2006.01)
*B01J 20/02* (2006.01)
*A61M 1/16* (2006.01)
*A61L 2/18* (2006.01)

(52) U.S. Cl.
CPC ............ *B01J 20/3475* (2013.01); *A61L 2/18* (2013.01); *A61M 1/169* (2013.01); *A61M 1/1696* (2013.01); *B01J 20/0211* (2013.01); *B01J 20/0292* (2013.01); *B01J 20/3433* (2013.01); *B01J 2220/62* (2013.01)

(58) Field of Classification Search
CPC .... B01J 20/34; B01J 20/0211; B01J 20/0292; B01J 20/3433; B01J 2220/62; A61L 2/18; A61M 1/169; A61M 1/1696
USPC ........................................................ 502/25
See application file for complete search history.

(56) References Cited

U.S. PATENT DOCUMENTS

| | | |
|---|---|---|
| 1,617,288 A | 2/1927 | Kenney |
| 3,608,729 A | 9/1971 | Haselden |
| 3,617,558 A | 11/1971 | Jones |
| 3,669,880 A | 6/1972 | Marantz |
| 3,776,819 A | 12/1973 | Williams |
| 3,840,835 A | 10/1974 | Kussy |
| 3,850,835 A | 11/1974 | Marantz |
| 3,884,808 A | 5/1975 | Scott |
| 3,902,490 A | 9/1975 | Jacobsen et al. |
| 3,989,622 A | 11/1976 | Marantz |
| 4,073,725 A | 2/1978 | Takeuchi |
| 4,094,775 A | 6/1978 | Mueller |
| 4,192,748 A | 3/1980 | Hyden |
| 4,206,054 A | 6/1980 | Moore |
| 4,209,392 A | 6/1980 | Wallace |
| 4,376,707 A | 3/1983 | Lehmann |
| 4,460,555 A | 7/1984 | Thompson |
| 4,581,141 A | 4/1986 | Ash |
| 4,650,587 A | 3/1987 | Polak |
| 4,661,246 A | 4/1987 | Ash |
| 4,684,460 A | 8/1987 | Issautier |
| 4,687,582 A | 8/1987 | Dixon |
| 5,230,702 A | 7/1993 | Lindsay et al. |
| 5,284,470 A | 2/1994 | Beltz |
| 5,302,288 A | 4/1994 | Meidl |
| 5,308,315 A | 5/1994 | Khuri |
| 5,507,723 A | 4/1996 | Keshaviah |
| 5,662,806 A | 9/1997 | Keshaviah et al. |
| 5,770,086 A | 6/1998 | Indriksons |
| 5,849,179 A | 12/1998 | Emerson |
| 5,858,186 A | 1/1999 | Glass |
| 5,944,684 A | 8/1999 | Roberts |
| 6,036,858 A | 3/2000 | Carlsson |
| 6,114,176 A | 9/2000 | Edgson et al. |
| 6,126,831 A | 10/2000 | Goldau et al. |
| 6,521,184 B1 | 2/2003 | Edgson et al. |
| 6,572,769 B2 | 6/2003 | Rajan |
| 6,579,460 B1 | 6/2003 | Willis |
| 6,627,164 B1 | 9/2003 | Wong |
| 6,666,840 B1 | 12/2003 | Falkvall et al. |
| 6,719,745 B1 | 4/2004 | Taylor |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,960,179 B2 | 11/2005 | Gura |
| 7,033,498 B2 | 4/2006 | Wong |
| 7,101,519 B2 | 9/2006 | Wong |
| 7,208,092 B2 | 4/2007 | Micheli |

(Continued)

FOREIGN PATENT DOCUMENTS

| | | |
|---|---|---|
| CN | 1487853 A | 4/2004 |
| CN | 102573618 | 7/2012 |

(Continued)

OTHER PUBLICATIONS

European Search Report for App. No. 20158130.3, dated Jul. 8, 2020.
European Search Report for EP18177683.2-1104 (dated Nov. 8, 2018).
European Search Report for EP18177673.3-1104 (dated Oct. 19, 2018).

(Continued)

*Primary Examiner* — Edward M Johnson

(57) ABSTRACT

The invention relates to systems and methods for disinfecting, recharging, and conditioning zirconium phosphate in a reusable sorbent module. The systems and methods provide for reuse of a zirconium phosphate sorbent module after dialysis.

23 Claims, 2 Drawing Sheets

(56) References Cited

U.S. PATENT DOCUMENTS

| | | |
|---|---|---|
| 7,241,272 B2 | 7/2007 | Karoor |
| 7,276,042 B2 | 10/2007 | Polaschegg |
| 7,326,576 B2 | 2/2008 | Womble et al. |
| 7,435,342 B2 | 10/2008 | Tsukamoto |
| 7,488,447 B2 | 2/2009 | Sternby |
| 7,537,688 B2 | 5/2009 | Tarumi et al. |
| 7,544,300 B2 | 6/2009 | Brugger et al. |
| 7,544,737 B2 | 6/2009 | Poss et al. |
| 7,563,240 B2 | 7/2009 | Gross et al. |
| 7,566,432 B2 | 7/2009 | Wong |
| 7,597,806 B2 | 10/2009 | Uchi |
| 7,794,419 B2 | 7/2010 | Paolini et al. |
| 7,776,210 B2 | 8/2010 | Rosenbaum |
| 7,850,635 B2 | 12/2010 | Polaschegg |
| 7,922,686 B2 | 4/2011 | Childers et al. |
| 7,922,911 B2 | 4/2011 | Micheli |
| 7,947,179 B2 | 5/2011 | Rosenbaum |
| 7,955,290 B2 | 6/2011 | Karoor et al. |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 10/2011 | Kelly et al. |
| 8,066,658 B2 | 11/2011 | Karoor et al. |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo et al. |
| 8,187,250 B2 | 5/2012 | Roberts |
| 8,197,439 B2 | 6/2012 | Wang et al. |
| 8,303,532 B2 | 11/2012 | Hamada et al. |
| 8,404,491 B2 | 3/2013 | Ding et al. |
| 8,409,444 B2 | 4/2013 | Wong |
| 8,480,607 B2 | 7/2013 | Davies |
| 8,647,506 B2 | 2/2014 | Wong |
| 8,733,559 B2 | 5/2014 | Wong |
| 8,764,981 B2 | 7/2014 | Ding |
| 8,777,892 B2 | 7/2014 | Sandford |
| 9,144,640 B2 | 9/2015 | Pudil |
| 9,254,355 B2 | 2/2016 | Sandford |
| 9,527,015 B2 | 12/2016 | Chau |
| 2001/0007931 A1 | 7/2001 | Blatter |
| 2002/0016550 A1 | 2/2002 | Sweeney |
| 2002/0112609 A1 | 8/2002 | Wong |
| 2003/0080059 A1 | 5/2003 | Peterson et al. |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | Thong |
| 2004/0019312 A1 | 1/2004 | Childers et al. |
| 2004/0099593 A1 | 5/2004 | DePaolis |
| 2004/0147900 A1 | 7/2004 | Polaschegg |
| 2004/0168963 A1 | 9/2004 | King |
| 2004/0257409 A1 | 12/2004 | Cheok |
| 2005/0006296 A1 | 1/2005 | Sullivan |
| 2005/0056592 A1 | 3/2005 | Braunger |
| 2005/0113796 A1 | 5/2005 | Taylor |
| 2005/0150832 A1 | 7/2005 | Tsukamoto |
| 2005/0234354 A1 | 10/2005 | Rowlandson |
| 2005/0274658 A1 | 12/2005 | Rosenbaum |
| 2006/0241543 A1 | 10/2006 | Gura |
| 2007/0007208 A1 | 1/2007 | Brugger et al. |
| 2007/0179431 A1 | 8/2007 | Roberts |
| 2007/0213665 A1 | 9/2007 | Curtin |
| 2008/0006570 A1 | 1/2008 | Gura |
| 2008/0011664 A1 | 1/2008 | Karoor |
| 2008/0051696 A1 | 2/2008 | Curtin |
| 2008/0053905 A9 | 3/2008 | Brugger et al. |
| 2008/0241031 A1 | 10/2008 | Li |
| 2009/0020471 A1 | 1/2009 | Tsukamoto |
| 2009/0078636 A1 | 3/2009 | Uchi |
| 2009/0101552 A1 | 4/2009 | Fulkerson |
| 2009/0120864 A1 | 5/2009 | Fulkerson |
| 2009/0216045 A1 | 8/2009 | Singh |
| 2009/0266358 A1 | 10/2009 | Sacristan Rock |
| 2009/0282980 A1 | 11/2009 | Gura |
| 2010/0004588 A1 | 1/2010 | Yeh |
| 2010/0007838 A1 | 1/2010 | Fujimoto |
| 2010/0078381 A1 | 4/2010 | Merchant |
| 2010/0078387 A1 | 4/2010 | Wong |
| 2010/0084330 A1 | 4/2010 | Wong |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114012 A1 | 5/2010 | Sandford |
| 2010/0217181 A1 | 8/2010 | Roberts |
| 2010/0224492 A1 | 9/2010 | Ding et al. |
| 2010/0312172 A1 | 12/2010 | Hoffman |
| 2010/0314314 A1 | 12/2010 | Ding |
| 2011/0009798 A1 | 1/2011 | Kelly |
| 2011/0017665 A1 | 1/2011 | Updyke |
| 2011/0048949 A1 | 3/2011 | Ding et al. |
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 | 11/2011 | Braig |
| 2011/0297593 A1 | 12/2011 | Kelly |
| 2012/0018377 A1 | 1/2012 | Tsukamoto |
| 2012/0248017 A1 | 10/2012 | Beiriger |
| 2012/0273354 A1 | 11/2012 | Orhan et al. |
| 2012/0303079 A1 | 11/2012 | Mahajan |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0158588 A1 | 6/2014 | Pudil |
| 2014/0158623 A1 | 6/2014 | Pudil |
| 2014/0190876 A1* | 7/2014 | Meyer .............. A61M 1/3406 210/87 |
| 2014/0190885 A1 | 7/2014 | Meyer |
| 2014/0217028 A1 | 8/2014 | Pudil |
| 2014/0251908 A1 | 9/2014 | Ding |
| 2014/0326671 A1 | 11/2014 | Kelly |
| 2015/0057602 A1 | 2/2015 | Mason |
| 2015/0108069 A1 | 4/2015 | Merchant |
| 2015/0108609 A1 | 4/2015 | Kushida |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0236188 A1 | 8/2016 | Menon |
| 2016/0243299 A1 | 8/2016 | Menon |
| 2016/0243540 A1 | 8/2016 | Menon |
| 2016/0243541 A1 | 8/2016 | Menon |
| 2018/0221852 A1 | 8/2018 | Pudil |

FOREIGN PATENT DOCUMENTS

| | | |
|---|---|---|
| CN | 105658326 A | 6/2016 |
| CN | 106413878 A | 2/2017 |
| EP | 711182 B1 | 6/2003 |
| EP | 1592494 B1 | 6/2009 |
| EP | 2575827 A2 | 12/2010 |
| EP | 2576453 A2 | 12/2011 |
| EP | 2446908 | 5/2012 |

(56) References Cited

FOREIGN PATENT DOCUMENTS

| | | |
|---|---|---|
| EP | 1545652 B1 | 1/2013 |
| EP | 1345856 B1 | 3/2013 |
| EP | 2344220 B1 | 4/2013 |
| EP | 3546042 | 10/2019 |
| EP | 3626280 | 3/2020 |
| JP | S5070281 A | 6/1975 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | H4-90963 | 5/2005 |
| JP | 2007-44602 A | 2/2007 |
| JP | 200744602 | 2/2007 |
| JP | 200744602 A | 2/2007 |
| JP | 2013502987 | 10/2013 |
| WO | 9532010 A1 | 11/1995 |
| WO | 0185295 A2 | 11/2001 |
| WO | 2002043859 | 6/2002 |
| WO | 2003043677 A2 | 5/2003 |
| WO | WO 2003041764 | 5/2003 |
| WO | 2003051422 A2 | 6/2003 |
| WO | 2004064616 A2 | 8/2004 |
| WO | 2004062710 A3 | 10/2004 |
| WO | 2005123230 A2 | 12/2005 |
| WO | 2007089855 A2 | 8/2007 |
| WO | 2008075951 A1 | 6/2008 |
| WO | 2009157877 A1 | 12/2009 |
| WO | 2009157878 A1 | 12/2009 |
| WO | 20090157877 | 12/2009 |
| WO | 2010028860 A1 | 3/2010 |
| WO | 2010102190 A4 | 11/2010 |
| WO | 2010141949 | 12/2010 |
| WO | WO 2011/017215 | 2/2011 |
| WO | 2013019179 | 2/2013 |
| WO | 2013019179 A1 | 2/2013 |
| WO | 2013025957 | 2/2013 |
| WO | 2013027214 | 2/2013 |
| WO | 2013028809 A3 | 2/2013 |
| WO | WO 2013/019179 | 2/2013 |
| WO | WO 2013/019994 | 2/2013 |
| WO | WO 2013-025957 | 2/2013 |
| WO | WO 2013-028809 | 2/2013 |
| WO | WO 2013019179 | 2/2013 |
| WO | WO2014121238 A1 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | WO 2013/103607 | 7/2013 |
| WO | WO 2013109922 | 7/2013 |
| WO | 2015060914 | 4/2015 |
| WO | WO 2015060914 | 4/2015 |
| WO | WO 2015/126879 | 8/2015 |
| WO | 2015142624 | 9/2015 |
| WO | 2015199764 | 12/2015 |
| WO | 2015199765 | 12/2015 |
| WO | 2015199863 | 12/2015 |
| WO | 2015199864 | 12/2015 |
| WO | WO 2015-199863 | 12/2015 |
| WO | WO 2015-199864 | 12/2015 |
| WO | WO 2015199765 | 12/2015 |
| WO | WO 2016/191039 | 12/2016 |
| WO | WO 2016/191041 | 12/2016 |

OTHER PUBLICATIONS

[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
[NPL162] International Search Report from PCT/US2012/051946 dated Mar. 4, 2013.
[NPL163] U.S. Appl. No. 61/526,209.
[NPL1] PCT/US2014/065950 International Search Report and Written Opinion dated Feb. 24, 2015.
[NPL238] PCT Application, PCT/US20013/020404, filed Jan. 4, 2013.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL247] U.S. Appl. No. 13/835,735, filed Mar. 15, 2013.
[NPL2] PCT/US2015/032492 International Search Report dated Nov. 19, 2015.
[NPL3] PCT/US2015/019901 International Search Report and Written Opinion dated Jun. 5, 2015.
[NPL494] John Wm Agar: Review: Understanding sorbent dialysis systems, Nephrology, vol. 15, No. 4, Jun. 1, 2010, pp. 406-411.
[NPL4] PCT/US2015/016270 International Search Report and Written Opinion dated Jun. 5, 2015.
[NPL548] PCT/US15/18587 International Preliminary Report on Patentability dated Jun. 6, 2016.
[NPL584] Office Action in App. No. AU 2015280604 dated Apr. 8, 2016 [NPL590].
PCT/US2016/030319 Written Opinion dated Jul. 27, 2016.
[NPL591] PCT/US2016/030320 Written Opinion dated Jul. 27, 2016.
[NPL5] PCT/US2015/016273 International Search Report and Written Opinion dated Jun. 9, 2015.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.
[NPL602] Office Action in App. No. JP 2016-515476 dated Dec. 26, 2016.
[NPL603] Japanese Patent Publication No. S50-70281A.
[NPL605] PCT/US2015/032494 Written Opinion dated Nov. 19, 2015.
[NPL606] PCT/US2015/032494 International Search Report dated Nov. 19, 2015.
[NPL607] PCT/US2015/019901 International Preliminary Report on Patentability dated May 27, 2016.
[NPL608] PCT/US2015/019901 Written Opinion dated May 27, 2016.
[NPL609] PCT/US2015/019901 Written Opinion dated Jun. 5, 2015.
[NPL610] PCT/US2015/019901 International Search Report dated Jun. 5, 2015.
[NPL611] PCT/US2015/032485 International Preliminary Report on Patentability dated May 11, 2016.
[NPL612] PCT/US2015/032485 International Preliminary Report on Patentability dated May 11, 2016.
[NPL613] PCT/US20115/032485 International Preliminary Report on Patentability dated May 11, 2016.
[NPL614] PCT/US2016/030304 International Search Report dated Jul. 27, 2016.
[NPL615] PCT/US2016/030304 Written Opinion dated Jul. 27, 2016.
[NPL616] PCT/US2016/030312 Written Opinion dated Jul. 28, 2016.
[NPL617] PCT/US2016/030312 International Search Report dated Jul. 28, 2016.
[NPL618] PCT/US2016/030319 International Search Report dated Jul. 27, 2016.
[NPL619] PCT/US2016/030319 Written Opinion dated Jul. 27, 2016.
[NPL620] PCT/US2016/030320 Written Opinion dated Jul. 28, 2016.
[NPL621] PCT/US2016/030320 International Search Report dated Jul. 28, 2016.
[NPL622] PCT/US2015/032485 Written Opinion dated Oct. 16, 2015.

(56) References Cited

OTHER PUBLICATIONS

[NPL623] PCT/US2015/032485 Written Opinion dated Oct. 16, 2016.
[NPL626] PCT/US2015/032485 International Search Report and Written Opinion dated Oct. 16, 2015.
[NPL634] PCT/US2016/030320 International Preliminary Report on Patentability, dated Apr. 20, 2017.
[NPL696] PCT/US2015/032485 Written Opinion dated May 9, 2016.
[NPL6] PCT/US2015/032492 Written Opinion dated Nov. 19, 2015.
[NPL720] PCT/US2015/019901 International Search Report and Written Opinion dated Jun. 5, 2015.
[NPL721] PCT/US2015/019901 International Preliminary Report on Patentability dated May 27, 2016.
[NPL722] PCT/US2015/032494 International Preliminary Report on Patentablity dated Dec. 27, 2016.
[NPL756] European Search Report and Supplemental Search Report in European Application No. 14865374.4 dated Jun. 12, 2017.
[NPL7] PCT/US2015/020046 International Search Report and Written Opinion dated Jun. 29, 2015.
[NPL8] PCT/US2015/020044 International Search Report Written Opinion dated Jun. 30, 2015.
[NPL] European Search Report App 14865374.4, dated Jun. 12, 2017.
European Search Report for App. No. 15812081.6, dated Mar. 8, 2018.
European Search Report for App. No. 18153940.4, dated Jun. 12, 2018.
European Search Report for EP App. No. 15811326.6, dated Feb. 14, 2018.
European Search Report for EP App. No. 15812413.1, dated Feb. 2, 2018.
Office Action in Japanese Application No. 2016-553344, dated Apr. 24, 2018.
PCT/US2016/030304_IPRP.
PCT/US2016/030319_IPRP.
Search Report for EP App. No. 17203984.4, dated Mar. 29, 2018.
Search Report in EP App. No. 15752771, dated Nov. 22, 2017.
Chinese Office Action for App. No. 201810580243.5, dated Jul. 3, 2020.
Chinese Office Action for App. No. 201711179528.X, dated Jul. 27, 2020.
European Search Report for App. No. 20164524.9, dated Aug. 21, 2020.

\* cited by examiner

ZIRCONIUM PHOSPHATE DISINFECTION RECHARGING AND CONDITIONING

CROSS-REFERENCE TO RELATED APPLICATIONS

This application claims the benefit of and priority to U.S. Provisional Patent Application No. 62/519,933 filed Jun. 15, 2017, the entire disclosure of which is incorporated by reference herein.

FIELD OF THE INVENTION

The invention relates to systems and methods for disinfecting, recharging, and conditioning zirconium phosphate in a reusable sorbent module. The systems and methods provide for reuse of a zirconium phosphate sorbent module after dialysis.

BACKGROUND

Zirconium phosphate containing sorbent cartridges are used in dialysis to remove ammonium, potassium, calcium, and magnesium ions from dialysate, allowing the dialysate to be reused. Known systems require zirconium phosphate to be removed from a sorbent cartridge, transported to a reprocessor, treated, and placed into a new sorbent cartridge, increasing costs and waste associated with reuse of zirconium phosphate. Known systems and methods also cannot reuse a zirconium phosphate sorbent module by concurrently disinfecting the zirconium phosphate to reduce the microbial load to acceptable levels, recovering the capacity of the zirconium phosphate, and conditioning the zirconium phosphate to an appropriate chemical state for dialysis. Hence, there is a need for systems and methods that can quickly and effectively disinfect, recharge and condition zirconium phosphate in a reusable sorbent module. There is further a need for systems and methods optimized to carry out all three steps with the least amount of waste at reduced cost than known systems and methods.

SUMMARY OF THE INVENTION

The first aspect of the invention relates to a method of recharging zirconium phosphate in a zirconium phosphate sorbent module. In any embodiment, the method can include flowing a disinfectant solution through the zirconium phosphate sorbent module; and flowing a brine solution through the zirconium phosphate sorbent module.

In any embodiment, the method can include the step of flowing water through the zirconium phosphate sorbent module after the steps of flowing disinfectant solution and brine solution through the zirconium phosphate sorbent module.

In any embodiment, the disinfectant solution can be a peracetic acid solution and the brine solution can contain acetic acid, sodium acetate, and sodium chloride.

In any embodiment, the brine solution can contain between 0 and 5.0 M sodium chloride, between 0.1 M and 2.0 M sodium acetate, and between 0.1 and 2.0 M acetic acid.

In any embodiment, the disinfection solution can contain between 0.1 to 3 wt % peracetic acid.

In any embodiment, the disinfection solution can contain between 0.1 to 3 wt % peracetic acid and between 0.1 to 15 wt % acetic acid.

In any embodiment, the step of flowing the disinfectant solution and the brine solution through the zirconium phosphate sorbent module can include flowing a mixture of the disinfectant solution and the brine solution through the zirconium phosphate sorbent module.

In any embodiment, the mixture of disinfectant solution and brine solution can be maintained at room temperature while flowing the mixture through the zirconium phosphate sorbent module.

In any embodiment, the mixture of disinfectant solution and brine solution can be maintained at room temperature for a set period of time, and then heated for a set period of time.

In any embodiment, the mixture of disinfectant solution and brine solution can have between 0.1 and 3.0 wt % peracetic acid, between 0 and 5.0 M sodium chloride, between 0.1 M and 2.0 M sodium acetate, and between 0.1 and 2.0 M acetic acid.

In any embodiment, the step of flowing a disinfectant solution through the zirconium phosphate sorbent module can include flowing a concentrated disinfectant solution and water to a static mixer to generate a dilute disinfectant solution; and flowing the dilute disinfectant solution through the zirconium phosphate sorbent module.

In any embodiment, the step of flowing a brine solution through the zirconium phosphate sorbent module can include flowing a concentrated brine solution and water to a static mixer to generate a dilute brine solution; and flowing the dilute brine solution through the zirconium phosphate sorbent module.

In any embodiment, the brine solution can be flowed through the zirconium phosphate sorbent module after the peracetic acid is flowed through the zirconium phosphate sorbent module.

In any embodiment, the peracetic acid solution can be flowed through the zirconium phosphate sorbent module after the brine solution is flowed through the zirconium phosphate sorbent module.

In any embodiment, the method can include the step of heating the brine solution prior to flowing the brine solution through the zirconium phosphate sorbent module.

In any embodiment, the brine solution can be heated to a temperature up to 100° C.

In any embodiment, the method can include flowing the brine solution to a static mixer and flowing the disinfectant solution to the static mixer prior to flowing the mixture of the disinfectant solution and the brine solution through the zirconium phosphate sorbent module.

In any embodiment, the step of flowing a mixture of the disinfectant solution and the brine solution through the zirconium phosphate sorbent module can include flowing the mixture from a combined disinfectant solution and brine solution source.

In any embodiment, the method can include rinsing the zirconium phosphate sorbent module with water prior to flowing the disinfectant solution through the zirconium phosphate sorbent module.

In any embodiment, the step of rinsing the zirconium phosphate sorbent module with water prior to flowing the disinfectant solution through the zirconium phosphate sorbent module can include flowing between 0.5 and 4.0 L, between 0.5 and 1.5 L, between 1.0 and 3.0 L, between 1.5 and 3.0 L, or between 2.0 and 4.0 L of water through the zirconium phosphate sorbent module.

In any embodiment, the method can include holding the disinfectant solution in the zirconium phosphate sorbent module.

In any embodiment, the disinfectant solution can be held in the zirconium phosphate sorbent module for between 0 and 30 minutes, between 5 and 10 minutes, between 5 and 15 minutes, between 10 and 20 minutes, between 15 and 30 minutes or between 20 and 30 minutes.

In any embodiment, the method can include flowing disinfectant solution through the zirconium phosphate sorbent module at a flow rate of between 0 and 20 mL/min while holding the disinfectant solution in the zirconium phosphate sorbent module.

In any embodiment, the method can include intermittently flowing fluid through the zirconium phosphate sorbent module while holding the disinfectant solution in the zirconium phosphate sorbent module.

In any embodiment, the method can include rinsing the zirconium phosphate sorbent module with water after flowing the disinfectant solution through the zirconium phosphate sorbent module and prior to flowing the brine solution through the zirconium phosphate sorbent module.

In any embodiment, the brine solution, the water, and the disinfectant solution can be flowed through the zirconium phosphate sorbent module in a direction opposite to a flow direction during therapy.

The features disclosed as being part of the first aspect of the invention can be in the first aspect of the invention, either alone or in combination.

The second aspect of the invention is drawn to a zirconium phosphate recharging flow path. In any embodiment, the zirconium phosphate recharging flow path can include (i) a water source and a combined disinfectant solution and brine solution source; (ii) a zirconium phosphate sorbent module inlet and a zirconium phosphate sorbent module outlet; wherein the zirconium phosphate sorbent module inlet and the zirconium phosphate sorbent module outlet are fluidly connectable to a zirconium phosphate sorbent module; (iii) at least one pump for flowing fluid from the water source and the combined disinfectant solution and brine solution source to the zirconium phosphate sorbent module inlet; and; (iv) a zirconium phosphate effluent line fluidly connectable to the zirconium phosphate sorbent module outlet.

In any embodiment, the combined disinfectant solution and brine solution source can contain between 0.1 and 3.0 wt % peracetic acid, between 0 and 5.0 M sodium chloride, between 0.1 M and 2.0 M sodium acetate, and between 0.1 and 2.0 M acetic acid.

In any embodiment, the zirconium phosphate recharging flow path can include a second pump.

In any embodiment, the zirconium phosphate recharging flow path can include a static mixer, the static mixer fluidly connected to the water source and the combined disinfectant solution and brine solution source.

The features disclosed as being part of the second aspect of the invention can be in the second aspect of the invention, either alone or in combination.

DETAILED DESCRIPTION OF THE INVENTION

Figure 1:
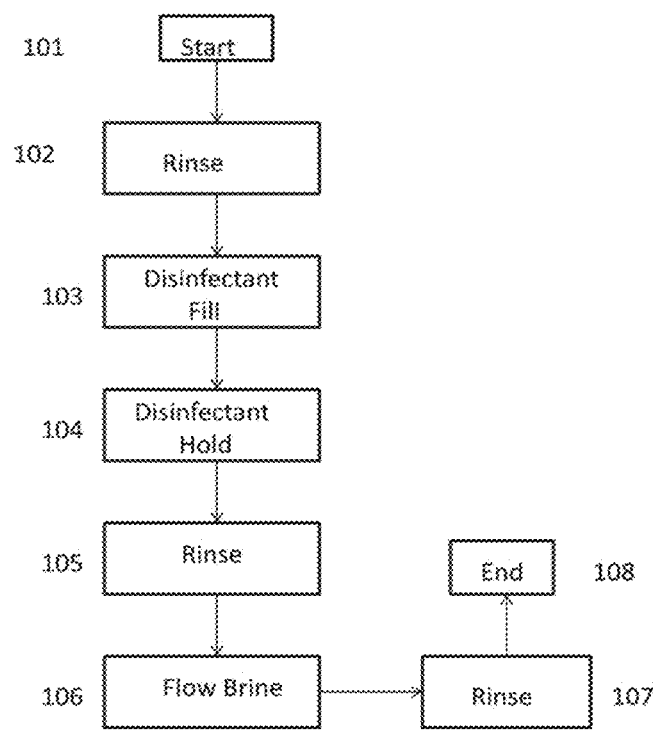
FIG. 1 is a flow chart of a method for disinfecting, recharging and conditioning zirconium phosphate.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The term "acetic acid" refers to $CH_3CO_2H$ in an aqueous solution.

A "brine solution" is a solution containing sodium chloride, an acid, and the sodium salt of the acid.

The term "combined disinfectant solution and brine solution source" refers to any source of a fluid containing both a disinfectant and a brine solution.

The term "comprising" includes, but is not limited to, whatever follows the word "comprising." Use of the term indicates the listed elements are required or mandatory but that other elements are optional and may be present.

A "concentrated" solution refers to a solution having at least one solute in a higher concentration than intended for use.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

A "dilute" solution refers to a concentrated solution after addition of a solvent to lower the solute concentration.

The term "direction opposite to a flow direction during therapy" refers to a direction of fluid flow through a component that is in reserver to an initial flow direction, or 180° to the initial direction of fluid flow, through the component during dialysis therapy.

The term "disinfectant solution" refers to any solution capable of destroying or removing bacterial contaminants from a reusable sorbent module.

The terms "flowing" or to "flow" "refer to the movement of a fluid, gas, or mixtures thereof.

The term "flow rate" refers to a volume of fluid moved in a flow path in a given period of time.

A "fluid" is a liquid substance optionally having a combination of gas and liquid phases in the fluid. Notably, a liquid, as used herein, can therefore also have a mixture of gas and liquid phases of matter.

The term "fluidly connectable," "fluidly connect," "for fluid connection," and the like, refer to the ability of providing for the passage of fluid, gas, or a combination thereof, from one point to another point. The two points can be within or between any one or more of compartments, modules, systems, components, and rechargers, all of any type. The connection can optionally be disconnected and then reconnected.

The term "generate" refers to creating a fluid with a specified concentration, pH, temperature, and/or volume from one or more fluid sources.

The term "heating" or to "heat" refers to raising the temperature of a material.

The term "holding a disinfectant solution" or to "hold a disinfectant solution" refers to adding a disinfectant solution to a component without immediate removal of the disinfectant solution. The term "holding a disinfectant solution" can also refer to flowing a disinfectant solution through the component at a low flow rate or an intermittent flow rate.

The term "intermittently" refers to a process that starts and stops multiple times.

The term "maintained at room temperature" or to "maintain at room temperature" refers to keeping a substance from increasing or decreasing in temperature substantially from room temperature.

The term "mixture" refers to a fluid having at least two components, the two components combined to form a substantially homogeneous substance.

The term "peracetic acid" refers to $CH_3CO_3H$ in an aqueous solution.

The term "peracetic acid solution" refers to a solution of peracetic acid, acetic acid and hydrogen peroxide The term "pump" refers to any device that causes the movement of fluids, gases, or combinations thereof, by applying suction or pressure.

"Recharging" refers to treating a sorbent material to restore the functional capacity of the sorbent material to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

The term "rinsing" or to "rinse" refers to flowing water through a component to remove substances from the component.

The term "room temperature" refers to the ambient temperature in an environment without additional heating or cooling. In general, room temperature can be considered between 15 and 30° C.

The term "set period of time" refers to a specific amount of time elapsed between two events.

The term "sodium acetate" refers to $CH_3CO_2Na$ in an aqueous solution.

The term "sodium chloride" refers to NaCl.

A "sorbent cartridge module" or "sorbent module" means a discreet component of a sorbent cartridge. Multiple sorbent cartridge modules can be fitted together to form a sorbent cartridge of two, three, or more sorbent cartridge modules. In some embodiments, a single sorbent cartridge module can contain all of the necessary materials for dialysis. In such cases, the sorbent cartridge module can be a "sorbent cartridge."

A "static mixer" is a component configured to receive fluids from one or multiple sources and to mix the fluids together. The static mixer may include components that agitate the fluids to further mixing.

The term "void volume" refers to a volume contained in a cartridge, not including a sorbent or any other material, through which liquid can flow. The term "void volume" can also refer to the volume of a cartridge or container available for a liquid or gas to fill the cartridge or container.

The term "water," as used herein, refers to $H_2O$ in a liquid state. "Water" can refer to portable water, drinking water, purified water, deionized water, tap water, or a solution containing one or more solutes dissolved in the water. The water shall not be limited to any specific purity, disinfection time, toxicity, microbial load, or any other indicator of water quality.

A "water source" is a fluid source from which water can be obtained.

"Zirconium phosphate" is a sorbent material that removes cations from a fluid, exchanging the removed cations for different cations.

A "zirconium phosphate effluent line" is a fluid passageway, tube, or path of any kind into which fluid exiting a zirconium phosphate sorbent module will flow.

A "zirconium phosphate module" or "zirconium phosphate sorbent module" is a sorbent module containing zirconium phosphate.

A "zirconium phosphate sorbent module inlet" is a connector through which a fluid, slurry, or aqueous solution can enter a zirconium phosphate sorbent module.

A "zirconium phosphate sorbent module outlet" is a connector through which a fluid, slurry, or aqueous solution can exit a zirconium phosphate sorbent module.

A "zirconium phosphate recharging flow path" is a path through which fluid can travel while recharging zirconium phosphate in a reusable zirconium phosphate sorbent module.

Zirconium Phosphate Recharging, Disinfection, and Conditioning

FIG. 1 is a flow chart illustrating a method for disinfecting, recharging, and conditioning zirconium phosphate. To reuse zirconium phosphate in dialysis, the method must achieve three steps. The cartridge must be disinfected to reduce the microbial load to acceptable levels, illustrated as disinfection steps 103-105; the capacity of the zirconium phosphate must be recovered, illustrated as recharging step 106; and the zirconium phosphate must be returned to an appropriate chemical state, or conditioned, which occurs during step 106-107.

The method of disinfecting the zirconium phosphate in a zirconium phosphate sorbent module can begin in step 101. During use in dialysis potassium, calcium, magnesium, and ammonium ions are adsorbed by the zirconium phosphate. In step 102, the zirconium phosphate sorbent module can be rinsed with water by flowing water through the zirconium phosphate sorbent module to remove any spent dialysate left in the module after therapy. The spent dialysate can have proteinaceous and other compounds that interact with the disinfectant used in subsequent steps. Rinsing the zirconium phosphate sorbent module with water removes the proteinaceous compounds. Any volume of water sufficient to remove the spent dialysate can be flowed through the zirconium phosphate sorbent module in step 102, including between 0.5 and 4.0 L, between 0.5 and 1.5 L, between 1.0 and 3.0 L, between 1.5 and 3.0 L, or between 2.0 and 4.0 L. In a preferred embodiment, about 1.0 L of water is flowed through the zirconium phosphate sorbent module in rinsing step 102. The rinse water can be flowed through the zirconium phosphate sorbent module at any temperature. In certain embodiments, the rinse water can be heated to aid in removal of spent dialysate or for pre-heating the zirconium phosphate sorbent module. Pre-heating the zirconium phosphate sorbent module can increase efficiency where the zirconium phosphate sorbent module may have been stored at low temperatures, such as 10° C. or less. The rinse water can be heated to any temperature between 20 and 100° C.

After rinsing the zirconium phosphate sorbent module, the zirconium phosphate sorbent module can be filled with a disinfectant solution in step 103. An aqueous peracetic acid solution can be the disinfectant solution. The peracetic acid solution can have any concentration of peracetic acid sufficient to disinfect the zirconium phosphate sorbent module, including between 0.1 and 5 wt %. In a preferred embodiment, the peracetic acid solution is 1 wt % in water. The volume of peracetic acid flowed into the zirconium phosphate sorbent module can be enough to fill the zirconium phosphate sorbent module, and can be between 100% to 200% or more of the void volume of the zirconium phosphate sorbent module. In a preferred embodiment, a volume of peracetic acid solution flowed into the zirconium phosphate sorbent module is 150% of the module void volume. With a 1.2 L zirconium phosphate sorbent module, 1.8 L of peracetic acid solution can be flowed into the module in step 103.

The peracetic acid solutions can be mixtures of peracetic acid, acetic acid and hydrogen peroxide. Typically, peracetic acid is the result of mixing acetic acid and hydrogen peroxide together, resulting in the generation of peracetic acid in equilibrium with the acetic acid and hydrogen peroxide. There are several varieties of peracetic acid solution available, which vary in the concentration of peracetic acid, acetic acid, and hydrogen peroxide. In addition to peracetic acid, the disinfectant solution can be a combined peracetic acid and acetic acid solution, which increases the effectiveness of the disinfection as compared to peracetic acid alone. The combined disinfectant and acid solution can contain between 0.1 and 3 wt % peracetic acid and 0.1 to 15 wt % acetic acid. Alternatively, hydrogen peroxide can be added to the peracetic acid, which increases the effectiveness of the disinfection as compared to peracetic acid alone. The addition of hydrogen peroxide can drive the equilibrium of peracetic acid, hydrogen peroxide, and acetic acid towards generation of peracetic acid as the initial peracetic acid is consumed. Further, both peracetic acid and hydrogen peroxide can be used as disinfectants alone. Both peracetic acid and hydrogen peroxide operate by oxidation, with each having an oxidation potential of 1.8 electron volts. Adding hydrogen peroxide to the peracetic acid solution can increase the total oxidation potential of the mixture, resulting in a more potent disinfectant. Chemical formulations including mixtures of peracetic acid and hydrogen peroxide are known. The mixtures can be clear, colorless liquids that are miscible with water. The mixtures can be oxidizing agents and disinfectants with a pungent odor, having peracetic acid, acetic acid, and hydrogen peroxide in equilibrium. Thermal decomposition of the mixtures occurs at temperatures above 60° C. Known compositions of peracetic acid and hydrogen peroxide solutions are available from Evonik, a German corporation. Examples of peracetic acid and hydrogen peroxide solutions include PERACLEAN® 5 having 5% peracetic acid and 26% hydrogen peroxide, PERACLEAN® 10 having 10% peracetic acid and 20% hydrogen peroxide, PERACLEAN® 15 having 15% peracetic acid and 21% hydrogen peroxide, PERACLEAN® 35 having 35% peracetic acid and 7% hydrogen peroxide, and PERACLEAN® 40 having 39% peracetic acid and 4% hydrogen peroxide. As the concentration of peracetic acid in the mixture is decreased, additional hydrogen peroxide can be added to increase effectiveness of the mixture. The formulations, or any other source of peracetic acid and hydrogen peroxide can be diluted to obtain a solution with desired concentrations of peracetic acid and hydrogen peroxide.

In step 104, the disinfectant solution can be held in the zirconium phosphate sorbent module for a sufficient length of time to ensure complete disinfection of the zirconium phosphate sorbent module. The hold time can be any length of time, including between 0 and 30 minutes, between 5 and 10 minutes, between 5 and 15 minutes, between 10 and 20 minutes, between 15 and 30 minutes or between 20 and 30 minutes. The length of the hold time can depend on the temperature of the zirconium phosphate sorbent module, and in a preferred embodiment the hold time can be 15 minutes at 22° C. Alternatively, the disinfectant solution can be heated in steps 103-104 to a temperature higher than 22° C., which increases the efficiency of disinfection. The disinfectant can be heated to any temperature, including between 22° C. and 100° C., between 22° C. and 50° C., between 22° C. and 35 C, between 30° C. and 50° C., between 35° C. and 65° C., between 50° C. and 75° C., or between 60° C. and 100° C. During step 104, a low flow rate of fluid through the zirconium phosphate sorbent module can be used to prevent pressure build up in the cartridge resulting from the degradation of peracetic acid. The low flow rate can vary from 1 to 20 ml/min. the low flow rate can have an on/off flow profile by intermittently switching the flow rate on and off while holding the disinfectant solution. The flow rate during the disinfectant hold can be set as 55 ml/min for 15 seconds and 0 ml/min for 45 seconds. In a preferred embodiment, the hold flow rate is 15 cycles of 55 ml/min for 15 seconds and 0-ml/min for 45 seconds.

In step 105, the zirconium phosphate module can be rinsed with water, allowing a buffer of water to be present between the peracetic acid solution and the subsequent brine solution. Step 105 is optional, and the method can proceed without rinsing between the peracetic acid step 104 and the brine step 106. When rinsing with water between steps 104 and 106, the volume of water used can vary between 0 and 1.0 L or more. In a preferred embodiment, step 105 is omitted. However, the zirconium phosphate module can be rinsed if material degradation to the cartridge housing or other components is detected. Material degradation may be an issue if the disinfectant used is a heated mixture of peracetic acid and acetic acid, or a mixture of peracetic acid and brine at temperatures around 80° C.

In step 106 a brine solution can be flowed through the zirconium phosphate sorbent module to recharge the zirconium phosphate. The brine solution can include an aqueous solution of sodium chloride, and acid, and the sodium salt of the acid. The brine solution provides additional disinfection of the zirconium phosphate; recovers the capacity of the zirconium phosphate by removing ammonium, potassium, calcium, and magnesium ions in exchange for sodium and hydrogen ions; and leaves the zirconium phosphate at the desired pH, or in the proper/desired sodium to hydrogen ion ratio for dialysis. Although FIG. 1 illustrates flowing the brine solution through the zirconium phosphate sorbent module in step 106 after flowing the disinfectant solution through the zirconium phosphate sorbent module in step 104, the order can be reversed, with the brine solution flowed through the zirconium phosphate module first, followed by the disinfectant solution. Flowing the disinfectant solution through the zirconium phosphate sorbent module after the brine solution can reduce the risk of the brine solution contaminating the cartridge. Further, the disinfectant solution can be kept in the zirconium phosphate sorbent module during storage, preventing microbial growth in the zirconium phosphate sorbent module during storage.

Any acid, sodium salt of an acid, and sodium salt can be used in the brine solution. In a preferred embodiment, the brine solution includes sodium chloride, acetic acid, and sodium acetate. However, the brine solution can be a glycolic/glycolate solution, a citric acid/citrate solution, a propionate/propionic acid solution, monobasic phosphate, or any combination thereof. The relative ratios of the acid and sodium salt of the acid in the brine solution can be varied depending on the desired zirconium phosphate pH. With a sodium acetate/acetic acid brine solution, the concentration of sodium chloride can vary between 0 and 5.0 M, the concentration of acetic acid can vary between 0.1 and 2.0 M, and the concentration of sodium acetate can vary between 0.1 and 2 M, where the upper concentration limits are only limited by solubility. The sodium chloride can be omitted in certain embodiments, and the zirconium phosphate sorbent module can be recharged with an acid and the sodium salt of the acid. The sodium salt of the acid can provide sodium ions and the acid can provide the hydrogen ions for recharging. The upper limit of the sodium salt and acid concentration is based on the solubility of the sodium salt and acid, and can depend on the type of sodium salt used and the acid concentration used. In a preferred embodiment, the brine solution contains about 4.854 M sodium chloride, 0.350 M sodium acetate, and 0.350 M acetic acid. Table 1 provides non-limiting examples of brine solutions and the resulting initial therapy zirconium phosphate effluent pH. In each case, the solution was heated to 80° C. prior to use. As shown in Table 1, a higher ratio of sodium acetate to acetic acid results in a higher solution pH, and therefore a higher initial therapy zirconium phosphate effluent pH. The relative amounts of acid, base, and sodium salt can be set to generate a brine solution resulting in a desired initial effluent pH.

TABLE 1

| Solution | Total Na (M) | NaCl (M) | NaAce (M) | HAce (M) | pH | Initial Effluent PH |
|---|---|---|---|---|---|---|
| 1 | 4.00 | 4.00 | 0.00 | 0.20 | 2.75 | 4.40 |
| 2 | 4.00 | 3.98 | 0.02 | 0.20 | 3.74 | 5.42 |
| 3 | 4.00 | 3.88 | 0.12 | 0.40 | 4.23 | 5.99 |
| 4 | 4.00 | 3.60 | 0.40 | 0.40 | 4.75 | 6.58 |

Each of the solutions in Table 1 are combinations of sodium chloride, sodium acetate, and acetic acid. One of skill in the art will understand that other combinations can be used in place of sodium acetate and acetic acid, including sodium diacetate. The sodium diacetate can be mixed with sodium acetate or acetic acid to result in a brine solution having a desired pH. Sodium diacetate and sodium acetate are solids, which may be easier to ship and store. The sodium diacetate and/or sodium acetate can be shipped and stored as a dry powder, eliminating the need to ship and handle acetic acid.

During step 106, the brine solution can optionally be heated. Heating the brine solution increases the efficiency of the recharging process. The brine solution can be heated to any temperature between 22 and 100° C., including between 22 and 40° C., between 22 and 60° C., between 35 and 50° C., between 45 and 70° C., between 55 and 85° C., between 60 and 90° C., between 75 and 85° C., or between 70 and 100° C. In a preferred embodiment, the brine solution is heated to about 80° C. during step 106. The brine solution can be used at lower temperatures with a decrease in efficiency.

The volume of brine solution to recharge the zirconium phosphate depends on the cations bound to the zirconium phosphate during therapy, and the size of the zirconium phosphate sorbent module, the temperature of the brine solution, and the concentrations of sodium chloride, acid, and sodium salt of the acid used in the brine solution. In a preferred embodiment, the volume of brine is 6.2 L for a zirconium phosphate sorbent module containing 2.69 kg of ZP with a capacity of 1 mEq cation per gram of ZP.

After flowing the brine solution through the zirconium phosphate sorbent module, the zirconium phosphate sorbent module can be rinsed in step 107 by flowing water through the zirconium phosphate sorbent module. The rinsing is necessary to remove the brine solution in the zirconium phosphate sorbent module to appropriate levels for storage and use during the next therapy session. The rinse water volume can vary from 100% to 500% of the cartridge void volume. In a preferred embodiment, the volume of rinse water is about 333% of the cartridge void volume, or 4 L for a zirconium phosphate sorbent module with a 1.2 L void volume. About 99% of the brine solution can be removed from the zirconium phosphate sorbent module during step 107, which leaves the zirconium phosphate sorbent module with an average concentration remaining of 52 mM total sodium, which is appropriate for storage and use during the next therapy session. The rinsing step 107 can occur during recharging of the zirconium phosphate sorbent module, or the zirconium phosphate sorbent module can be rinsed in the dialysis system just prior to use. Rinsing the zirconium phosphate sorbent module just prior to use allows the disinfectant solution, if the disinfectant step is performed after the brine step, to remain in the zirconium phosphate sorbent module during storage, reducing microbial growth. The method can end in step 108, with a zirconium phosphate sorbent module in condition for reuse in dialysis. Alternatively, the zirconium phosphate module can be fully or partially drained after recharging and conditioning for storage, which decreases the weight and exposure to water during storage.

The direction of flow of brine through the zirconium phosphate sorbent module during step 106 can be in a direction opposite to a flow direction during therapy. During therapy, spent dialysate enters the bottom of the module, flows upwards against gravity, and exits the top of the cartridge. During recharging the brine can enter the zirconium phosphate sorbent module at the top and exit through the bottom, flowing with gravity. Alternatively, the spent dialysate flow direction during therapy can be downward, and the brine can flow upwardly through the zirconium phosphate sorbent module during recharging. The rinse and disinfection flow direction during steps 102-105 and 107 can be either the same or opposite to the flow direction during therapy. Alternatively, the direction of flow of brine during recharging can be the same as the flow direction during therapy, however, flowing brine through the zirconium phosphate module in the same direction as flow during therapy may require additional brine volume for recharging. In a preferred embodiment, the rinse and disinfection flow direction is the same direction as the brine flow direction.

Figure 2:
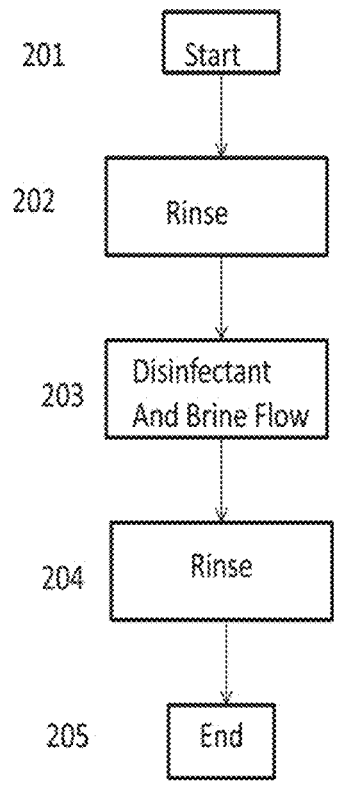
FIG. 2 is a flow chart of a method for disinfecting, recharging and conditioning zirconium phosphate with a combined disinfection and recharging solution.

FIG. 2 illustrates an alternative embodiment of the disinfection, recharging, and conditioning of zirconium phosphate. The method can start in step 201. In step 202, the zirconium phosphate sorbent module can be rinsed with water by flowing water through the zirconium phosphate sorbent module to remove any spent dialysate left in the module after therapy. In step 203 a mixture of disinfectant solution and brine can be flowed through the zirconium phosphate sorbent module. The disinfectant solution can be added to the brine, and the process for recharging, disinfecting, and conditioning the zirconium phosphate sorbent module can be similar to the process illustrated in FIG. 1, allowing disinfection, capacity recovery, and conditioning in one step. The mixture of disinfectant solution and brine disinfects and recharges the zirconium phosphate in a single step, as opposed to separate steps as illustrated in FIG. 1. The concentrations of peracetic acid, sodium chloride, sodium acetate, and acetic acid in the mixture can be the same as the individual solutions shown in FIG. 1. The mixture of brine and peracetic acid may help stabilize the peracetic acid in the disinfectant solution because the presence of the acetate buffer keeps the peracetic acid/acetic acid equilibrium shifted to the peracetic acid side. During step 203, the mixture of peracetic acid and brine can be held in the zirconium phosphate sorbent module for any length of time sufficient to ensure complete disinfection or alternatively, the mixture of peracetic acid and brine can be continuously flowed through the zirconium phosphate sorbent module. In a preferred embodiment, the mixture of peracetic acid and brine is heated to about 80° C. in step 203, however the solutions may alternatively be at a lower, unheated temperature, such as room temperature. The mixture of peracetic acid and brine can be heated to any temperature between 22 and 100° C., including between 22 and 40° C., between 22 and 60° C., between 35 and 50° C., between 45 and 70° C., between 55 and 85° C., between 60 and 90° C., between 75 and 85° C., or between 80 and 100° C. Alternatively, the mixture of peracetic acid and brine can be kept at room temperature for a set period of time to ensure complete disinfection, and then heated for a set period of time to increase the efficiency of the recharging process. The mixture of peracetic acid and brine solution can be maintained at room temperature for 5-30 minutes, and then subsequently heated. In a preferred embodiment, about 6.2 L of a solution of 1 wt % peracetic acid and the brine solutions described can be flowed through the zirconium phosphate sorbent module at about 80° C. In step 204, the zirconium phosphate sorbent module can be rinsed by flowing water through the zirconium phosphate sorbent module to remove the brine and peracetic acid solution in the zirconium phosphate sorbent module to appropriate levels for storage and use during the next therapy session. The method can end in step 205 with a zirconium phosphate sorbent module in condition for reuse in dialysis.

Figure 3:
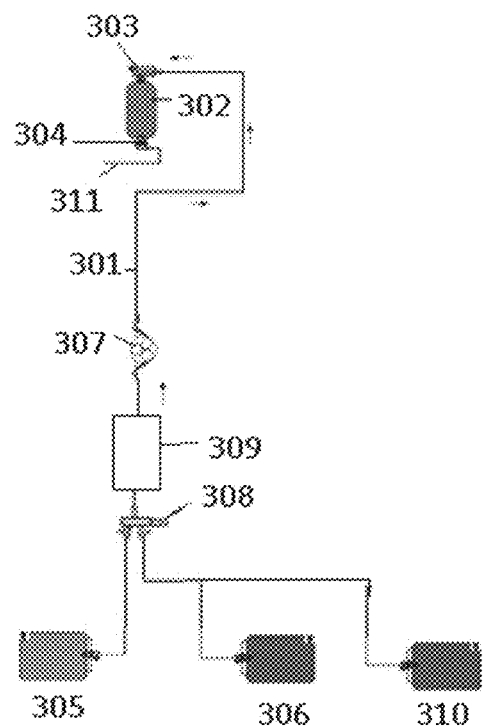
FIG. 3 is a flow path for disinfection, recharging and conditioning of zirconium phosphate in a reusable sorbent module.

FIG. 3 illustrates a non-limiting embodiment of a flow path for disinfecting, recharging, and conditioning of a zirconium phosphate sorbent module 302. A zirconium phosphate sorbent module 302 can connect to the zirconium phosphate recharging flow path 301 through zirconium phosphate sorbent module inlet 303 and zirconium phosphate sorbent module outlet 304. A zirconium phosphate effluent line 311 can be fluidly connected to the zirconium phosphate sorbent module outlet 304 for removal of solutions after the solutions pass through the zirconium phosphate sorbent module 302. Pump 307 provides a driving force for flowing fluids through the zirconium phosphate recharging flow path 301. A brine source 305, containing a sodium salt and buffer, such as sodium chloride, sodium acetate, and acetic acid is fluidly connected to the zirconium phosphate recharging flow path 301. Disinfectant source 306 can contain a disinfectant solution, such as peracetic acid. Water source 310 is also fluidly connected to the zirconium phosphate recharging flow path 301. The water source 310 can contain any water as defined herein, including deionized water. The water can be obtained from a tap such as a faucet or from any other readily available source in a home setting. Water obtained from a tap is not limited to any specific country requirements and contemplates various water specifications insofar as various countries may have different requirements. In general, the water should not be contaminated by infectious agents, toxic chemicals, or radiological hazards. The water can comport with WHO requirements for potable or drinking water. However, the invention contemplating water from many sources having various purity and quality levels and requirements, shall not be limited in such respects. Valve 308 controls the movement of fluid through the zirconium phosphate recharging flow path 301 and zirconium phosphate sorbent module 302. A static mixer 309 can optionally be included to ensure complete mixing of solutions prior to entering the zirconium phosphate sorbent module 302. For example, when a mixture of brine and peracetic acid is used for single step disinfecting and recharging, the static mixer 309 ensures that the peracetic acid and brine are mixed to generate a dilute mixture of brine and peracetic acid for simultaneous recharging and disinfection. One of skill in the art will understand that different pump and valve arrangements can be used with the system illustrated in FIG. 3. The brine source 305, disinfectant source 306, and water source 310 can be connected to the zirconium phosphate recharging flow path 301 through separate pumps, allowing simultaneous addition of water, brine, and disinfectant to the zirconium phosphate recharging flow path 301.

The zirconium phosphate recharging flow path 301 can flow solutions through the zirconium phosphate sorbent module 302 in a sequential order or simultaneously. As illustrated in FIG. 1, the zirconium phosphate recharging flow path 301 can flow water, disinfectant, brine, and water again through the zirconium phosphate sorbent module 302 sequentially. The zirconium phosphate recharging flow path 301 can flow water through the zirconium phosphate sorbent module 302, followed by simultaneously flowing peracetic acid and brine through the zirconium phosphate sorbent module 302 as illustrated in FIG. 2.

The solutions in the brine source 305 and disinfectant source 306 can be any concentration, including the concentrations shown in FIGS. 1-2. The solutions in brine source 305 and/or disinfectant source 306 can be concentrated solutions. The brine solution can have sodium chloride, acid, and sodium salt of the acid at concentrations higher than that to be used in recharging the zirconium phosphate sorbent module 302. The brine solution and water can be simultaneously flowed to static mixer 309 to dilute the concentrated brine solution in the recharging steps generating a dilute brine solution usable for recharging the zirconium phosphate. Similarly, a concentrated disinfectant solution and water can be simultaneously flowed to static mixer 309 to dilute the disinfectant solution during the disinfecting steps, generating a dilute disinfectant solution for disinfecting the zirconium phosphate. A heater and/or heat exchanger (not shown) can be included for heating the brine solution, the disinfectant solution, and/or the rinse water prior to flowing the solutions through the zirconium phosphate sorbent module 302.

Figure 4:
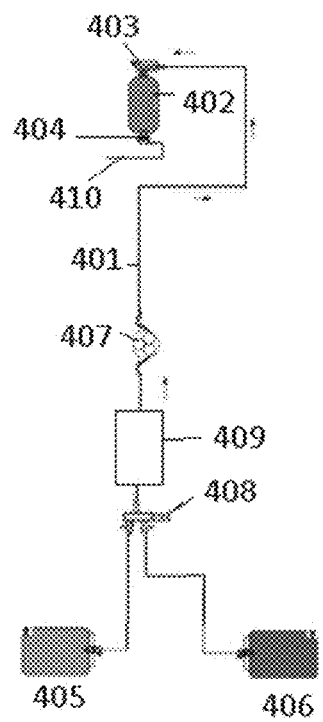
FIG. 4 is a flow path for disinfection, recharging and conditioning of zirconium phosphate using a combined disinfection and recharging solution.

FIG. 4 illustrates a non-limiting embodiment of a flow path for disinfecting, recharging, and conditioning of a zirconium phosphate sorbent module 402 with a combined brine and disinfectant fluid, as illustrated in FIG. 2. A zirconium phosphate sorbent module 402 can connect to the zirconium phosphate recharging flow path 401 through zirconium phosphate sorbent module inlet 403 and zirconium phosphate sorbent module outlet 404. A zirconium phosphate effluent line 410 can be fluidly connected to the zirconium phosphate sorbent module outlet 404 for removal of solutions after the solutions pass through the zirconium phosphate sorbent module 402. Pump 407 provides a driving force for flowing fluids through the zirconium phosphate recharging flow path 401. A combined disinfectant solution and brine solution source 405, containing a sodium salt and buffer, such as sodium chloride, sodium acetate, and acetic acid, and a disinfectant such as peracetic acid, can be fluidly connected to the zirconium phosphate recharging flow path 401. Water source 406 is also fluidly connected to the zirconium phosphate recharging flow path 401. Valve 408 controls the movement of fluid through the zirconium phosphate recharging flow path 401 and zirconium phosphate sorbent module 402. A static mixer 409 can optionally be included to ensure complete mixing of solutions prior to entering the zirconium phosphate sorbent module 402 and can generate a dilute solution from the combined disinfectant solution and brine solution source 405 when a concentrated solution is used. One of skill in the art will understand that different pump and valve arrangements can be used with the system illustrated in FIG. 4. For example, the combined disinfectant solution and brine solution source 405 and water source 406 can be connected to the zirconium phosphate recharging flow path 401 through separate pumps, allowing simultaneous addition of water, brine, and disinfectant to the zirconium phosphate recharging flow path 401. A heater and/or heat exchanger (not shown) can be included for heating the combined disinfectant solution and brine solution and/or the rinse water prior to flowing the solutions through the zirconium phosphate sorbent module 402.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A method of recharging zirconium phosphate in a zirconium phosphate sorbent module, comprising the steps of:
   flowing a combined disinfectant and brine solution through the zirconium phosphate sorbent module from a combined disinfectant solution and brine solution source fluidly connected to a zirconium phosphate recharging flow path;
   wherein the zirconium phosphate recharging flow path comprises:
   i. a water source and a combined disinfectant solution and brine solution source;
   ii. a zirconium phosphate sorbent module inlet and a zirconium phosphate sorbent module outlet; wherein the zirconium phosphate sorbent module inlet and the zirconium phosphate sorbent module outlet are fluidly connectable to a zirconium phosphate sorbent module;
   iii. at least one pump for flowing fluid from the water source and the combined disinfectant solution and brine solution source to the zirconium phosphate sorbent module inlet; and
   iv. a zirconium phosphate effluent line fluidly connectable to the zirconium phosphate sorbent module outlet;
   wherein the combined disinfectant solution and brine solution source comprises at least peracetic acid, sodium chloride, and acetic acid.

2. The method of claim 1, further comprising the step of flowing water through the zirconium phosphate sorbent module after the step of flowing the combined disinfectant and brine solution through the zirconium phosphate sorbent module.

3. The method of claim 1, wherein the combined disinfectant and brine solution contains peracetic acid, acetic acid, sodium acetate, and sodium chloride.

4. The method of claim 3, wherein the combined disinfectant and brine solution contains between 0 and 5.0 M sodium chloride, between 0.1 M and 2.0 M sodium acetate, and between 0.1 and 2.0 M acetic acid.

5. The method of claim 3, wherein the combined disinfectant and brine solution contains between 0.1 and 3.0 wt % peracetic acid.

6. The method of claim 3, wherein the combined disinfectant and brine solution contains between 0.1 and 3.0 wt % peracetic acid and between 0.1 to 15 wt % acetic acid.

7. The method of claim 1, wherein the combined disinfectant and brine solution is maintained at room temperature while flowing the combined disinfectant and brine solution through the zirconium phosphate sorbent module.

8. The method of claim 1, wherein the combined disinfectant and brine solution is maintained at room temperature for a set period of time, and then heated for a set period of time.

9. The method of claim 1, wherein the combined disinfectant and brine solution comprises between 0.1 and 3.0 wt % peracetic acid, between 0 and 5.0 M sodium chloride, between 0.1 M and 2.0 M sodium acetate, and between 0.1 and 2.0 M acetic acid.

10. The method of claim 1, wherein the step of flowing the combined disinfectant and brine solution through the zirconium phosphate sorbent module comprises flowing a concentrated combined disinfectant and brine solution and water to a static mixer to generate a dilute combined disinfectant and brine solution; and flowing the dilute combined disinfectant and brine solution through the zirconium phosphate sorbent module.

11. The method of claim 1, further comprising the step of heating the combined disinfectant and brine solution prior to flowing the combined disinfectant and brine solution through the zirconium phosphate sorbent module.

12. The method of claim 11, wherein the combined disinfectant and brine solution is heated to a temperature of between 70° C. and 100° C.

13. The method of claim 1, further comprising the step of rinsing the zirconium phosphate sorbent module with water prior to flowing the combined disinfectant and brine solution through the zirconium phosphate sorbent module.

14. The method of claim 13, wherein the step of rinsing the zirconium phosphate sorbent module with water prior to flowing the combined disinfectant and brine solution through the zirconium phosphate sorbent module comprises flowing between 0.5 and 4.0 L, between 0.5 and 1.5 L, between 1.0 and 3.0 L, between 1.5 and 3.0 L, or between 2.0 and 4.0 L of water through the zirconium phosphate sorbent module.

15. The method of claim 1, further comprising the step of holding the combined disinfectant and brine solution in the zirconium phosphate sorbent module.

16. The method of claim 15, wherein the combined disinfectant and brine solution is held in the zirconium phosphate sorbent module for between 0 and 30 minutes, between 5 and 10 minutes, between 5 and 15 minutes, between 10 and 20 minutes, between 15 and 30 minutes or between 20 and 30 minutes.

17. The method of claim 15, further comprising the step of flowing combined disinfectant and brine solution through the zirconium phosphate sorbent module at a flow rate of between 0 and 20 mL/min while holding the combined disinfectant and brine solution in the zirconium phosphate sorbent module.

18. The method of claim 15, further comprising the step of intermittently flowing fluid through the zirconium phosphate sorbent module while holding the combined disinfectant and brine solution in the zirconium phosphate sorbent module.

19. The method of claim 2, wherein the combined disinfectant and brine solution and the water are flowed through the zirconium phosphate sorbent module in a direction opposite to a flow direction during therapy.

20. A zirconium phosphate recharging flow path, comprising:
   i. a water source and a combined disinfectant solution and brine solution source;
   ii. a zirconium phosphate sorbent module inlet and a zirconium phosphate sorbent module outlet; wherein the zirconium phosphate sorbent module inlet and the zirconium phosphate sorbent module outlet are fluidly connectable to a zirconium phosphate sorbent module;
   iii. at least one pump for flowing fluid from the water source and the combined disinfectant solution and brine solution source to the zirconium phosphate sorbent module inlet; and
   iv. a zirconium phosphate effluent line fluidly connectable to the zirconium phosphate sorbent module outlet;
   wherein the combined disinfectant solution and brine solution source comprises at least peracetic acid, sodium chloride, and acetic acid.

21. The zirconium phosphate recharging flow path of claim 20, wherein the combined disinfectant solution and brine solution source comprises between 0.1 and 3.0 wt % peracetic acid, between 0 and 5.0 M sodium chloride, between 0.1 M and 2.0 M sodium acetate, and between 0.1 and 2.0 M acetic acid.

22. The zirconium phosphate recharging flow path of claim 20, further comprising at least a second pump.

23. The zirconium phosphate recharging flow path of claim 22, further comprising a static mixer, the static mixer fluidly connected to the water source and the combined disinfectant solution and brine solution source.

\* \* \* \* \*